US008222200B2

(12) United States Patent
Flachsmann et al.

(10) Patent No.: US 8,222,200 B2
(45) Date of Patent: Jul. 17, 2012

(54) ORGANIC COMPOUNDS

(75) Inventors: Felix Flachsmann, Zürich (CH); Jean-Pierre Bachmann, Wädenswil (CH)

(73) Assignee: Givaudan SA, Vernier (CH)

( * ) Notice: Subject to any disclaimer, the term of this patent is extended or adjusted under 35 U.S.C. 154(b) by 1381 days.

(21) Appl. No.: 10/552,655

(22) PCT Filed: Apr. 14, 2004

(86) PCT No.: PCT/CH2004/000227
§ 371 (c)(1),
(2), (4) Date: Oct. 11, 2005

(87) PCT Pub. No.: WO2004/089880
PCT Pub. Date: Oct. 21, 2004

(65) Prior Publication Data
US 2006/0270588 A1 Nov. 30, 2006

(30) Foreign Application Priority Data

Apr. 14, 2003 (GB) .................................. 0308512.3
Apr. 15, 2003 (GB) .................................. 0308686.5

(51) Int. Cl.
| A61K 8/18 | (2006.01) |
| A61K 8/00 | (2006.01) |
| A61Q 13/00 | (2006.01) |
| C07C 229/00 | (2006.01) |
| C07C 205/00 | (2006.01) |
| C07C 261/00 | (2006.01) |
| C07C 269/00 | (2006.01) |
| C07C 271/00 | (2006.01) |
| A61Q 5/00 | (2006.01) |
| A61Q 9/00 | (2006.01) |

(52) U.S. Cl. ................... 512/26; 512/1; 512/10; 560/19; 560/20; 560/115; 424/70.1

(58) Field of Classification Search .............. 512/26, 512/10, 1; 560/19, 115, 20; 514/29; 424/71, 424/70.1; 442/153
See application file for complete search history.

(56) References Cited

U.S. PATENT DOCUMENTS

| 2,060,733 A * | 11/1936 | Hunt et al. .................. 442/153 |
| 2,197,479 A * | 4/1940 | Meigs .......................... 560/166 |
| 2,460,291 A * | 2/1949 | Hunt ............................ 568/875 |
| 2,517,965 A * | 8/1950 | Bohl ............................ 558/266 |
| 3,203,853 A * | 8/1965 | Jager et al. ................... 514/481 |
| 3,336,368 A | 8/1967 | Schweirsch et al. |
| 3,966,903 A * | 6/1976 | Torii et al. .................. 424/70.4 |
| 4,260,526 A * | 4/1981 | Kaiser et al. ................... 512/9 |
| 4,382,765 A * | 5/1983 | Moller et al. ................ 514/788 |
| 4,772,695 A | 9/1988 | Olofson et al. |
| 4,900,834 A | 2/1990 | Kruger et al. |
| 5,472,946 A * | 12/1995 | Peck et al. ..................... 514/29 |
| 6,399,808 B1 * | 6/2002 | Jung ............................... 560/19 |
| 2001/0036907 A1 * | 11/2001 | Finch et al. .................. 510/101 |
| 2003/0065213 A1 | 4/2003 | Zofchak |

FOREIGN PATENT DOCUMENTS

| DE | 960896 | * | 3/1957 |
| DE | 3312498 | | 10/1984 |
| EP | 591054 A1 | * | 4/1994 |
| EP | 952142 A1 | | 10/1999 |
| GB | 1116005 | | 6/1968 |
| WO | WO 01/94438 A | | 12/2001 |
| WO | WO0194438 A1 | * | 12/2001 |

OTHER PUBLICATIONS

Eddy et al. J. Econ. Ent. vol. 39 No. 66 pp. 763-767 1946.*
P-ethoxybenzaldehyde MAKEMEHEAL Produc Dat sheet id-45175 http://www.makemeheal.com/mmh/product.do?id=45175.*
Graniol the Good Scents Company {http:www.thegoodscentscompany.com/data/rw1006991.html}.*
Matthew T. Hancock and Allan R. Pinhas, "A convenient and inexpensive conversion of an aziridine to an oxazolidinone", *Tetrahedron Letters* (2003), 5457-5460.
International Search Report dated Jul. 20, 2004 for application PCT/CH2004/000227.
Search Report dated Sep. 10, 2003 from the Patent Office in Great Britain for application GB 0308512.3.
Search Report dated Sep. 19, 2003 from the Patent Office in Great Britain for application GB 0308686.5.
Written Opinion of the International Searching Authority for application PCT/CH2004/000227.
Chemical Abstracts, 1948 vol. 42, 7717-c-i.
Chemical Abstracts, 1959, vol. 53, 3128i, 3129a-e.
English language abstract of DE 960896.
English language abstract of JP 63280052.

* cited by examiner

*Primary Examiner* — Patrick Ryan
*Assistant Examiner* — Aaron Greso
(74) *Attorney, Agent, or Firm* — Norris McLaughlin & Marcus PA

(57) ABSTRACT

Tertiary non-vinylic carbamates of molecular weight less than 350 are useful as fragrance ingredients. A method of preparation is also described.

9 Claims, No Drawings

ORGANIC COMPOUNDS

This invention relates to tertiary carbamates and their use as fragrance ingredients. It furthermore relates to a method of making them and their use in fragrance compositions.

There is an ongoing need for powerful new perfumery ingredients which are stable towards aggressive media to which they are exposed. Surprisingly, we have found that certain tertiary non-vinylic carbamates, which have olfactory properties useful for perfumery, are stable against hydrolysis over a wide range of pH and towards oxidation. With the exception of N- or O-vinyl carbamates, tertiary carbamates constitute valuable ingredients for the perfumery industry. O- and N-vinyl carbamates, in analogy to enol esters and enamides, are susceptible to acid-catalyzed hydrolysis. Furthermore, in accordance with their use as monomers in the polymer industry, they polymerize easily. The aforementioned tertiary non-vinylic carbamates exhibit odors in the spicy, herbaceous or floral-rosy range with excellent substantivity and are useful as fragrance ingredients.

The use as fragrance ingredients of tertiary non-vinylic carbamates, i.e. non-vinylic carbamic acid ester of the formula

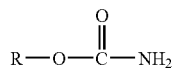

wherein the hydrogen atoms covalently bonded to the nitrogen atom are substituted, has not been previously described in the literature.

Thus, the present invention refers in a first aspect to the use as fragrance ingredients of tertiary non-vinylic carbamates, i.e. tertiary carbamates having no N-vinyl or O-vinyl substituent, having a molecular weight less than 350, preferably a molecular weight not higher than 300.

In a preferred embodiment, the present invention refers to the use as a fragrance ingredient of a N,N-substituted carbamate having a group covalently bonded to the ether oxygen atom of the carbamate, selected from the group consisting of alkyl, alk-(>1)-enyl, alkynyl, cycloalkyl, cycloalkenyl, phenyl, naphthyl, cycloalkylalkyl, cycloalkenylalkyl, phenylalkyl and naphtylalkyl, said covalently-bonded group being optionally substituted with alkyl, alkenyl and alkoxy, and said group optionally comprising heteroatoms, for example oxygen, nitrogen or sulphur.

More particularly, the present invention refers to the use as fragrance ingredients of tertiary carbamates of formula (I)

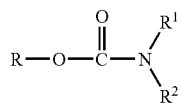

wherein
$R^1$ and $R^2$ are independently selected from the group consisting of:
(a) $C_1$ to $C_{11}$ alkyl, preferably $C_1$ to $C_6$ alkyl, e.g. methyl, ethyl, propyl, iso-propyl; $C_3$ to $C_{11}$ alk-(>1)-enyl, preferably $C_3$ to $C_6$ alkenyl, e.g. prop-2-enyl; or $C_2$ to $C_{11}$ alkynyl group; and
(b) cycloalkyl optionally substituted with alkyl, alkenyl and alkoxy group(s); $C_3$ to $C_8$ cycloalkenyl optionally substituted with alkyl, alkenyl and alkoxy group(s); or phenyl or naphthyl, wherein the aromatic ring is optionally substituted with alkyl, alkenyl and alkoxy group(s); and
(c) $C_4$ to $C_{14}$ cycloalkylalkyl, wherein the cycloalkyl ring is optionally substituted with alkyl, alkenyl and alkoxy group(s); or phenylalkyl or naphthylalkyl, wherein the aromatic ring is optionally substituted with alkyl, alkenyl and alkoxy group(s); and
R is selected from the group consisting of:
(a) $C_1$ to $C_{11}$ alkyl; $C_3$ to $C_{11}$ alk-(>1)-enyl; or $C_2$ to $C_{11}$ alkynyl group; and
(b) cycloalkyl optionally substituted with alkyl, alkenyl, and alkoxy group(s); $C_3$ to $C_8$ cycloalkenyl optionally substituted with alkyl, alkenyl and alkoxy group(s); or phenyl or naphthyl optionally substituted with alkyl, alkenyl and alkoxy group(s); and
(c) $C_4$ to $C_{14}$ cycloalkylalkyl, wherein the cycloalkyl ring is optionally substituted with alkyl, alkenyl and alkoxy group(s); $C_4$ to $C_{14}$ cycloalkenylalkyl, wherein the cycloalkenyl ring is optionally substituted with alkyl, alkenyl and alkoxy group(s); or phenylalkyl or naphthylalkyl, wherein the aromatic ring is optionally substituted with alkyl, alkenyl and alkoxy group(s); and
(d) $C_5$ to $C_{14}$ cycloalkylalkoxyalkyl, wherein the cycloalkyl ring is optionally substituted with alkyl, alkenyl and alkoxy group(s); $C_5$ to $C_{14}$ cycloalkenylalkoxyalkyl, wherein the cycloalkenyl ring is optionally substituted with alky, alkenyl and alkoxy group(s); or phenylalkoxyalkyl or naphthylalkoxyalkyl, wherein the aromatic ring is optionally substituted with alkyl, alkenyl and alkoxy group(s); and
(e) heteroaromatic ring, e.g. pyridyl, furyl; heteroarylalkyl ring, e.g. furylmethyl, pyridylmethyl, pyridylethyl; heterocyclic ring, e.g. dihydrofuryl, tetrahydrofuryl; or heterocycloalkyl ring, e.g. dihydrofurylmethyl, tetrahydrofurylmethyl, wherein the ring is optionally substituted with alkyl, alkenyl and alkoxy group(s), the ring having 5 to 6 ring members, and the hetero atom is oxygen or nitrogen; and
R, $R^1$ and $R^2$ having together 7 to 18 carbon atoms, more preferably 7 to 16 carbon atoms, most preferably 8 to 12; or
$R^1$ is selected from the group consisting of:
(a) $C_1$ to $C_6$ alkyl; $C_3$ to $C_5$ alk-(>1)-enyl; or $C_2$ to $C_5$ alkynyl group; and
(b) $C_3$ to $C_6$ cycloalkyl optionally substituted with alkyl and alkenyl group(s); $C_3$ to $C_6$ cycloalkenyl optionally substituted with alkyl and alkenyl group(s); or phenyl optionally substituted with allyl and alkenyl group(s); and
(c) $C_4$ to $C_8$ cycloalkylalkyl, wherein the cycloalkyl ring is optionally substituted with alkyl and alkenyl group(s); or phenyl alkyl, wherein the aromatic ring is optionally substituted with alkyl and alkenyl group(s); and
R and $R^2$ form together with the atom to which they are attached a 5 to 8 membered heterocyclic ring, which is optionally substituted with alkyl and alkenyl group(s); and R, $R^1$ and $R^2$ having together 7 to 18 carbon atoms, more preferably 7 to 16 carbon atoms, most preferably 8 to 12.

As used in relation to compounds of formula (I) unless otherwise indicated "cycloalkyl" refers to $C_3$ to $C_8$, preferably $C_4$ to $C_6$, e.g. cyclopentyl, cyclohexyl; "alkyl" refers to linear or branched $C_1$ to $C_5$ alkyl, e.g. n-pentyl, sec-pentyl, tert-pentyl, n-butyl, sec-butyl, tert-butyl, preferably $C_1$ to $C_3$, e.g. methyl, ethyl, i-propyl; "alkenyl" refers to vinyl or linear or branched $C_3$ to $C_5$ alkenyl, e.g. propen-1-yl, propen-2-yl, allyl, and but-2-en-1-yl; "alk-(>1)-enyl" refers to $C_3$ to $C_{11}$ linear or branched alkenyl in which there is at least one sp³-hybridised C-atom between the N-atom or ether oxygen atom of the carbamate and the nearest C—C double bond, e.g. hex-3-en-1-yl, 3-methyl-but-2-en-1-yl; and "alkoxy" refers to $C_1$ to $C_4$, such as methoxy, ethoxy, and isopropoxy.

By the term "optionally substituted", as used in relation to compounds of formula (I) is meant that there is no substitutent, or there is at least one substituent, for example one or more alkyl group(s), one or more alkenyl group(s), or one or more alkoxy group(s), or a combination of at least two substituents, e.g. an alkyl group and an alkoxy group, two alkyl groups and one alkenyl group, one alkyl group and one alkenyl group.

Preferred are compounds according to formula (I), wherein $R^1$ and $R^2$ together have 2 to 13 carbon atoms, more preferably 2 to 9 carbon atoms, most preferably 2 to 6 carbon atoms. Compounds according to the present invention wherein $R^1=R^2$ are also preferred.

The compounds of formula (I) may comprise one or more chiral centres and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC or by stereoselective syntheses.

Whereas some compounds of the formula (I) have been described in the literature, others have not, and are novel.

Thus, in a second aspect of the invention, there is provided a compound of formula (I) wherein R, $R^1$ and $R^2$ are selected according to the following table:

| R | $R^1$ | $R^2$ |
|---|---|---|
| hex-3-enyl | ethyl | ethyl |
| 2-ethyl-hexyl | methyl | methyl |
| methyl | ethyl | methyl-tolyl |
| methyl | ethyl | ethyl-tolyl |
| 3-methyl-but-2-enyl | ethyl | ethyl |
| 3-methyl-but-3-enyl | ethyl | ethyl |
| hex-3-enyl | methyl | iso-propyl |
| 2,2,5-trimethyl-hex-4-enyl | ethyl | ethyl |
| undec-10-enyl | methyl | methyl |
| 2-ethyl-hexyl | methyl | iso-propyl |
| 2-ethyl-hexyl | ethyl | iso-propyl |
| R and $R^1$ together with the atoms to which they are attached is 4-Methyl-oxazolidyl-2-one | | pentyl |
| 1,1-dimethyl-(4-methyl-cyclohex-3-enyl)-ethyl | methyl | methyl |
| 1,1-dimethyl-(4-methyl-cyclohex-3-enyl)-methyl | methyl | methyl |
| ethyl | methyl | hexyl |
| 2-methyl-propyl | methyl | butyl |
| 2-methyl-propyl | ethyl | butyl |
| 1,2-dimethyl-1-propyl-propyl | methyl | methyl |
| 1,2-dimethyl-1-propyl-iso-propyl | methyl | methyl |
| 2-ethoxy-phenyl | methyl | methyl |
| 2-[1-(3,3-dimethyl-cyclohexyl)-ethoxy]-2-methyl-propyl | methyl | methyl |
| 2-[1-(3,3-dimethyl-cyclohexyl)-ethoxy]-2-methyl-propyl | ethyl | ethyl |
| furylmethyl | ethyl | ethyl |

The compounds according to the present invention may be used alone or in combination with known odourant molecules selected from the extensive range of natural and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odourants in fragrance compositions, for example, carrier materials, and other auxiliary agents commonly used in the art.

The following list comprises examples of known odourant molecules, which may be combined with the compounds of the present invention:
- ethereal oils and extracts, e.g. castoreum, costus root oil, oak moss absolute, geranium oil, jasmin absolute, patchouli oil, rose oil, sandalwood oil or ylang-ylang oil;
- alkohols, e.g. citronellol, Ebanol™, eugenol, geraniol, Super Muguet™, linalool, phenylethyl alcohol, Sandalore™, terpineol or Timberol™.
- aldehydes and ketones, e.g. α-amylcinnamaldehyd, Georgywood™, hydroxycitronellal, Iso E Super®, Isoraldeine®, Hedione®, maltol, methyl cedryl ketone, methylionone or vanillin;
- ether and acetals, e.g. Ambrox™, geranyl methyl ether, rose oxide or Spirambrene™.
- esters and lactones, e.g. benzyl acetate, cedryl acetate, γ-decalactone, Helvetolide®, γ-undecalactone or vetivenyl acetate.
- macrocycles, e.g. ambrettolide, ethylene brassylate or Exaltolide®.
- heterocycles, e.g. isobutylchinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odourant ingredients. The proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in an alcoholic solution in amounts of from 0.1 to 20 weight percent, more preferably between 0.1 and 5 weight percent. However, these values are given only by way of example, since the experienced perfumer may also achieve effects or may create novel accords with lower or higher concentrations.

The compounds of the present invention may be employed into the fragrance application simply by directly mixing the fragrance composition with the fragrance application, or they may, in an earlier step be entrapped with an entrapment material such as for example polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation as a fragrance ingredient of a tertiary carbamate having a molecular weight less than 350.

Linear N,N-dialkylcarbamate compounds of formula (I), i.e. compounds of formula (I) wherein R and $R^2$ together with the atoms to which they are attached do not form a ring, may be synthesised by reacting the corresponding chloroformic acid alkyl ester of formula (IV) e.g. chloroformic acid hex-3-enyl ester, with the corresponding dialkylamine of formula (III), e.g. diethylamine, or they may be synthesised by reacting the corresponding dialkyl carbamoyl chloride of formula (II), e.g. dimethyl carbamoyl chloride, with the corresponding alcohol ROH, e.g. 2,3,4-trimethyl-pentan-3-ol, as shown in Scheme 1. The appropriate method to use depends mainly on the availability of the starting materials. Other routes may also be used, for example, the reaction of an alcohol ROH with an N-alkylisocyanates, as known to a person skilled in the art, and described for example in DE 3312498.

Scheme 1:

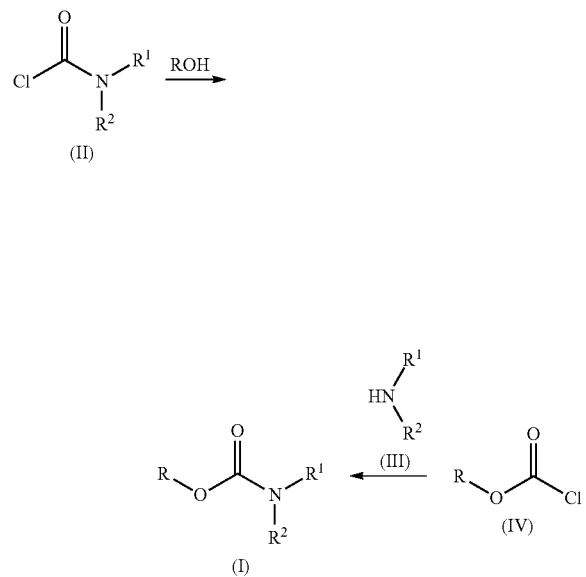

Furthermore, linear N,N-dialkylcarbamate compounds of formula (I) may be synthesised by a two step process by reacting the corresponding primary amine, e.g. isopropylamine, with the corresponding chloroformic acid alkyl ester of formula (IV), e.g. chloroformic acid 2-ethyl hexyl ester, in the presence of one mole equivalent of a base, for example NaH, resulting in the corresponding secondary carbamate of formula (V) in a first step. Further alkylation of the secondary carbamate by adding the corresponding alkylating agent, e.g. alkyltoluene sulfonates, alkylmethane sulfonates, dialkyl sulfates (for example dimethyl sulfate), and alkyl halides, in the presence of one mole equivalent of a base, for example NaH, results in the corresponding linear $N_1N$-dialkylcarbamate compounds of formula (I), as shown in Scheme 2.

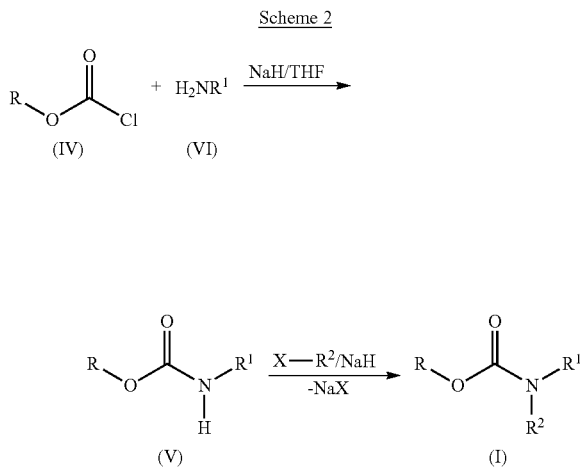

The process according to Scheme 2 is particularly useful for the production of non-symmetrical N,N-dialkylcarbamate compounds of formula (I), i.e. compounds according to the present invention wherein $R^1$ is different from $R^2$. Using the two-step process has the advantage that such non-symmetrical N,N-dialkylcarbamate compounds may be synthesised in one reaction vessel without isolating the intermediate.

Thus, a further aspect of the present invention is a process for the production of a compound of formula (I) by (a) reacting a primary amine of formula (VI) in the presence of a base, e.g. NaH with a chloroformic acid alkyl ester of formula (IV) to give a secondary carbamate of formula (V), and then (b) reacting the secondary carbamate of formula (V) in the presence of a base, e.g. NaH with an alkylating agent of the formula $R^2$—X, wherein X is $Br^-$, $Cl^-$, $I^-$, or $R^4$—$SO^4$, wherein $R^4$ is methyl or tolyl, and wherein R, $R^1$ and $R^2$ are as hereinabove defined, and step (a) and (b) are sequentially carried out in the same reaction vessel.

Cyclic carbamate compounds of formula (I), i.e. wherein R and $R^2$ together with the atoms to which they are attached form a ring, may be synthesised by reaction of dialkyl carbonate, e.g. diethyl carbonate and dimethyl carbonate, with the corresponding primary amino-alcohol, e.g. 2-aminopropanol, in the presence of alkali alcoholate, e.g. sodium ethanolate, followed by alkylation of the resulting secondary amine, which results in the cyclic tert. carbamate of formula (I). Cyclic carbamate compounds of formula (I) may also be synthesised by ring-closing metathesis reaction of carbamate bridged diolefins as well known to the person skilled in the art.

The invention is now further described with reference to the following non-limiting examples.

EXAMPLE 1

Diethyl-carbamic acid hex-3-enyl ester (Table 1. compound No1)

Diethylamine (9.1 g, 125 mmol, 1.25 equiv.) was added to a 2%-aqueous NaOH-solution (200 ml) and the resulting mixture was cooled to 0° C. (icebath). At this temperature chloroformic acid hex-3-enyl ester (16.2 g, 100 mmol) in diethyl ether (200 ml) was added over a period of 35 min. After complete addition, the cooling bath was removed and stirring was continued for 1.5 h. The mixture was acidified with 2N aqueous HCl-solution, the phases separated and the organic phase was washed with brine and dried over $MgSO_4$. The crude product was purified via fractionated distillation (74-76° C./0.05 mbar) to yield 18.2 g (92%) of product.

IR (film): 2967 w, 1698 vs, 1272 s, 1171 s, 1072 m, 770 m. $^1$H-NMR (400 MHz, $CDCl_3$): 5.50-5.46 (m, 1H), 5.37-5.33 (m, 1H), 4.07 (t, J=7, 2H), 3.30 (br. s, 4H), 2.39 (q, J=7, 2H), 2.07 (quint, J=7, 2H), 1.11 (t, J=7, 6H), 1.00 (t, J=8, 3H). $^{13}$C-NMR: 155.9 (s), 133.9 (d), 124.2 (d), 64.4 (t), 41.5/41.1 (br. t, 2 rotamers), 27.1 (t), 20.4 (t), 14.1 (q), 13.8/13.4 (br. q, 2 rotamers). MS (EI 70 eV): 199 (<1%, M+), 118 (100), 100 (45, 82 (39), 72 (33), 67 (55), 55 (68).

Odor description: green, peppery, liquorice

Further compounds as listed in Table 1 were prepared according to the procedure described above.

TABLE 1

| No. | Structure | yield | $^{13}$C—NMR-data (400 MHz, CDCl$_3$) | MS* | Olfactory description |
|---|---|---|---|---|---|
| 1 | 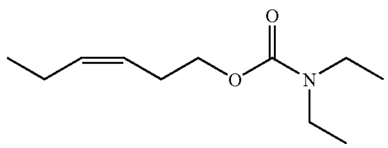 | 92% | 155.9 (s), 133.9 (d), 124.2 (d), 64.4 (t), 41.5/41.1(br. t, 2 rotamers), 27.1 (t), 20.4 (t), 14.1 (q), 13.8/13.4 (br. q, 2 rotamers) | 199 | green peppery, liquorice |
| 2 | 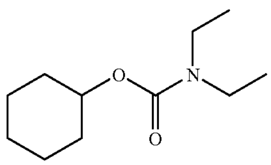 | 57% | 155.5 (s), 72.4 (d), 41.3 (br. t), 31.8 (d), 25.4 (d), 23.5(d), 13.7 (br. q) | 199 | floral, minty, terpenyl acetate |
| 3 | 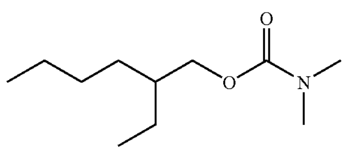 | 92% | 156.8 (s), 67.6 (t), 38.9 (d), 36.1/35.6 (br. q, 2 rotamers), 30.3 (t), 28.8 (t), 23.7 (t), 22.8 (t), 13.8 (q), 10.9 (q) | 201 | anisic, floral, spicy |
| 4 | 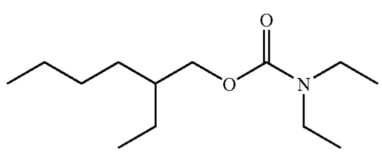 | 78% | 156.1 (s), 67.1 (t), 41.3 (br. t), 39.0 (d), 30.4 (t), 28.8 (t), 23.8 (t), 22.8 (t), 13.9 (q), 13.6 (br. q), 10.9 (q) | 229 | green, woody, spicy, vetyver, gaïac |
| 5 | 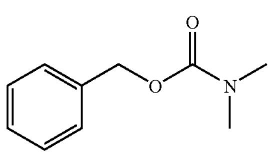 | 25% | 156.3 (s), 136.9 (s), 128.3 (d), 127.8 (d), 127.7 (d), 66.9 (t), 36.3/35.8 (br. q, 2 rotamers) | 179 | fruity, rosy |
| 6 | 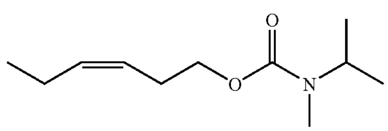 | 77% | 156.0 (s), 134.0 (d), 124.1 (d), 64.5 (t), 46.2 (d), 27.1 (t), 20.4 (t), 19.6 (br. q), 14.1 (q) | 199 (118) | peach, veloutone, nectaryl |
| 7 | 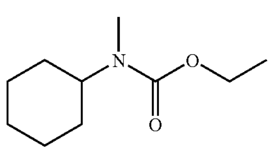 | 70% | 156.2 (s), 60.8 (t), 54.5 (br. d), 30.1 (br. t), 28.0 (br. q), 25.6 (d), 25.4 (d), 14.6 (q) | 185 (142) | mushroom, minty, herbal |
| 8 | 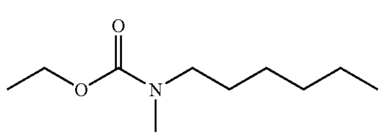 | 71% | 156.4 (s), 60.8 (t), 48.8/48.4 (br. t, 2 rotamers), 34.2/33.6 (br. q, 2 rotamers), 31.4 (t), 27.6/27.3(br. t, 2 rotamers), 26.1 (t), 22.4 (t), 14.6 (q), 13.8 (q) | 187 (116) | floral, green, jasmin |
| 9 | 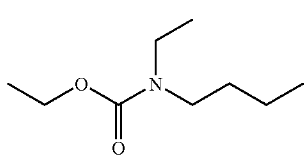 | 57% | 156.0 (s), 60.5 (t), 46.4/45.8 (br. t, 2 rotamers), 41.6/41.4 (br. t, 2 rotamers), 30.6/30.3 (br. t, 2 rotamers), 19.7 (t), 14.4 (q), 13.6 (q), 13.1 (br. q) | 173 (130) | celery, jasmine |
| 10 | 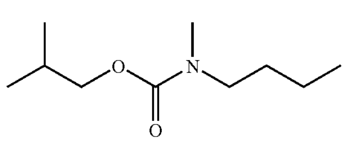 | 59% | 156.5 (s), 71.2 (t), 48.5/48.3 (br. t, 2 rotamers), 34.3/33.6 (br. q, 2 rotamers), 30.0/29.5 (br. t, 2 rotamers), 27.9 (d), 19.7 (t), 19.0 (q), 13.7 (q) | 187 (57) | floral, leather |

TABLE 1-continued

| No. | Structure | yield | $^{13}$C—NMR-data (400 MHz, CDCl$_3$) | MS* | Olfactory description |
|---|---|---|---|---|---|
| 11 | 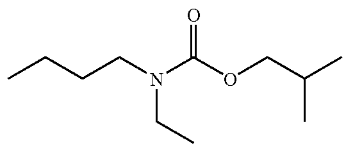 | 49% | 156.2 (s), 71.0 (t), 46.6/46.1 (br. t, 2 rotamers), 41.9/41.5 (br. t, 2 rotamers), 30.8/30.4 (br. t, 2 rotamers), 27.9 (d) 19.9 (t), 19.0 (q), 13.7 (q), 13.8/13.2 (br. q, 2 rotamers) | 201 (57) | floral, fruity, medicinal, woody |
| 13 | 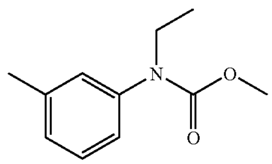 | 30% | 155.8 (s), 141.5 (s), 138.8 (s), 128.6 (d), 127.9 (d), 127.4 (d), 124.3 (d), 52.6 (q), 45.3 (t), 21.2 (q), 13.5 (q) | 193 | fruity, green, rosy |

*: molecular ion; in parentheses: 100% signal

EXAMPLE 2

Dimethyl-carbamic acid 1-isopropyl-1,2-dimethyl-propyl ester (Table 2, Compound 24)

A solution of 2,3,4-Trimethyl-pentan-3-ol (13.0 g, 100 mmol, 1 equiv.) in toluene (50 ml) was added to a suspension of NaH (55% in mineral oil, 4.80 g, 110 mmol, 1.1 equiv.) in toluene (50 ml). The mixture was heated to 100° C. for 1 h, then cooled to 0° C. A solution of dimethyl carbamoyl chloride (12.9 g, 120 mmol, 1.2 equiv.) in toluene (30 ml) was added over 45 min. The resulting suspension was stirred at room temperature for 19 h, then diluted with MTBE and worked up as describe in Example 1. Distillation of the crude at 0.05 mbar/52-61° C. yielded 61% of product.

IR (film): 2967 m, 1698 vs, 1379 s, 1196 s, 868 m, 769 m.
$^1$H-NMR (400 MHz, CDCl$_3$): 2.88 (br. s, 6H), 2.31 (hept, J=7, 2H), 1.41 (s, 3H), 0.97 (d, J=7, 6H), 0.94 (d, J=7, 6H).
$^{13}$C-NMR: 156.0 (s), 88.9 (s), 36.0 (q), 34.5 (d), 18.3 (q), 18.1 (q), 17.9 (s). MS (EI 70 eV): 186 (<1%, [M-1]$^+$), 158 (4), 112 (37), 97 (67), 72 (71), 69 (72), 55 (100), 44 (83).

Odour description: fruity, rosy, spicy

Further compounds were prepared following the synthesis protocol above are listed In Table 2.

TABLE 2

| No. | Structure | yield | $^{13}$C—NMR-data (400 MHz, CDCl$_3$) | MS* | Olfactory description |
|---|---|---|---|---|---|
| 12 (trans: cis = 3:1) | | 75% | (major trans diastereomer) 156.3 (s), 74.2 (d), 47.0 (d), 36.0/35.6 (br. q, 2 rotamers), 32.5 (t), 27.4 (d), 25.3 (t) | 227 | woody, fruity, vertenex type |
| 14 | 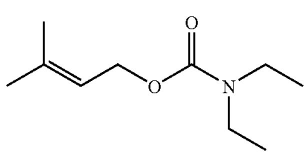 | 37% | 156.0 (s), 137.4 (s), 119.6 (d), 61.8 (t), 41.5/41.1 (br. t, 2 rotamers), 25.6 (q), 17.9 (q), 13.7/13.4 (br. q, 2 rotamers) | 197 | celery, spicy, animalic |
| 15 | 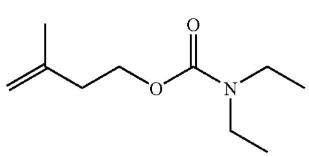 | 83% | 155.8 (s), 142.0 (s), 111.8 (d), 63.0 (t), 41.5/41.1 (br. q, 2 rotamers), 37.1 (t), 22.3 (q), 13.8/13.4 (br. q, 2 rotamers) | 185 (102) | salicylate, quinoline, green, earthy |
| 16 | 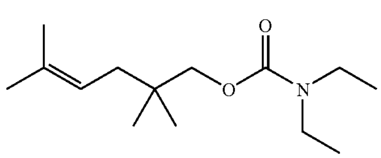 | 98% | 156.0 (s), 133.4 (s), 120.1 (d), 72.8 (t) 41.6/41.1 (br. t, 2 rotamers), 37.2 (t), 35.0 (s), 25.9 (q), 24.1 (q), 17.6 (q), 14.0/13.4 (br. q, 2 rotamers) | 124 (M-HCO$_2$NEt$_2$), (109) | fruity, rosy, spicy |

TABLE 2-continued

| No. | Structure | yield | $^{13}$C—NMR-data (400 MHz, CDCl$_3$) | MS* | Olfactory description |
|---|---|---|---|---|---|
| 17 | 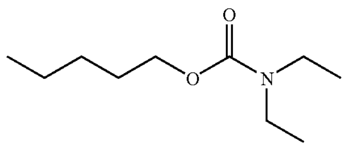 | 75% | 156.0 (s), 64.9 (t), 41.5/41.1 (br. t, 2 rotamers), 28.6 (t), 28.0 (t), 22.2 (t), 13.8 (q), 13.7/13.4 (br. q, 2 rotamers) | 187 (43) | celery, jasminic |
| 18 | 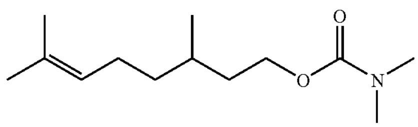 | 57% | 156.7 (s), 131.0 (s), 124.5 (d), 63.7 (t), 36.8 (t), 36.2/35.6 (br. q, 2 rotamers), 35.8 (t), 29.3 (d), 25.5 (q), 25.2 (t), 19.3 (q), 17.5 (q) | 227 (81) | rosy, pear, apricot |
| 19 | 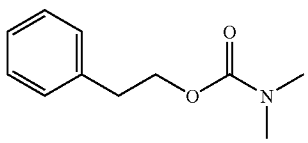 | 45% | 156.4 (s), 138.1 (s), 128.8 (d), 128.3 (d), 126.4 (d), 65.7 (t), 36.2 (br. q), 35.6 (br. q), 35.5 (t) | 193 (104) | balsamic, spicy, rosy |
| 20 | 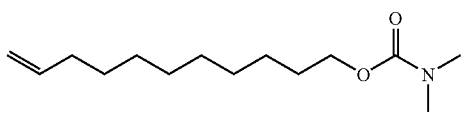 | 63% | 156.7 (s), 139.0 (d), 114.0 (t), 65.3 (t), 36.2 (br. q), 35.6 (br. q), 33.6 (t), 29.3 (t), 29.2 (t), 29.1 (t), 28.9 (t), 28.8 (t), 25.8 (t) | 241 (90) | green, orange blossom, rosy, woody |
| 21 | E/Z = 3:2 | 21% | (only E) 156.7 (s), 140.9 (s), 131.5 (s), 123.7 (d), 119.2 (d), 62.0 (t), 39.4 (t), 36.2/35.7 (br. q, 2 rotamers), 26.2 (t), 25.5 (q), 17.5 (q), 16.3 (q) | 225 (69) | fruity, rosy |
| 22 | 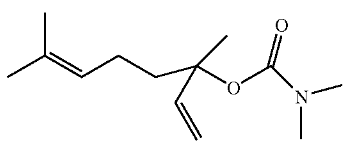 | 50% | 155.3 (s), 142.7 (d), 131.4 (s), 123.9 (d), 112.3 (t), 81.8 (s), 40.2 (t), 35.9 (q), 25.5 (q), 23.8 (q), 22.3 (t), 17.4 (q) | 225 (93) | woody, agarwood, olibanum, vetyver, peppery |
| 23 | 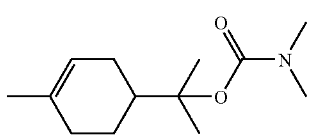 | 50% | 155.8 (s), 133.7 (s), 120.4 (d), 83.4 (s), 43.2 (d), 35.9 (br. q), 30.8 (t), 26.3 (t), 23.9 (t), 23.5 (q), 23.5 (q), 23.2 (q) | 210 (M-CH$_3$) (68) | fruity, gaïacwood |
| 24 | 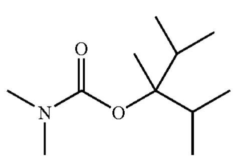 | 46% | 156.0 (s), 88.9 (s), 36.0 (q), 34.5 (d), 18.3 (q), 18.1 (q), 17.9 (s) | 186 (M-CH$_3$) (55) | fruity, rosy, spicy |
| 25 | 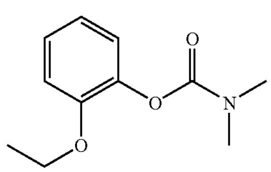 | 59% | 154.8 (s), 150.8 (s), 141.0 (s), 126.0 (d), 123.1 (d), 120.5 (d), 113.5 (d), 64.2 (t), 36.6 (q), 36.4 (q), 14.7 (q) | 209 (72) | spicy, eugenol, animalic, smokey |
| 26 | 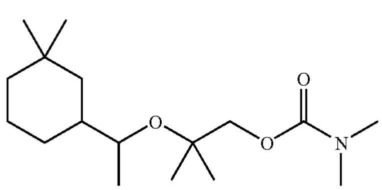 | 42% | 156.4 (s), 77.2 (s), 71.5 (d), 71.0 (t), 42.1 (t), 40.2 (d), 39.2 (t), 36.2/35.7 (br. q, 2 rotamers), 33.5 (q), 30.5 (s), 28.1 (t), 24.5 (q), 24.1 (q), 22.1 (q), 19.7 (t), 19.6 (q) | 197 (M-C$_4$H$_8$NO$_2$) (72) | musk |

*: molecular ion; in parentheses: 100% signal

EXAMPLE 3

Isopropyl-methyl-carbamic acid 2-ethyl-hexyl ester

A solution of isopropylamine (2.95 g, 50 mmol, 1 equiv.) was added at RT to a suspension of NaH (55% in mineral oil, 2.40 g, 55 mmol, 1.1 equiv.) in THF (25 ml). The mixture was warmed to 40° C. for 18 h, then chloroformic acid 2-ethyl-hexyl ester in THF (25 ml) was added dropwise over 30 min. After 4 h further stirring a suspension of NaH (55% in mineral oil, 2.40 g, 55 mmol, 1.1 equiv.) in THF (25 ml) was added followed by a solution of dimethyl sulfate (5.2 ml, 55 mmol, 1.1 equiv.) in THF (20 ml). The mixture was heated to 70° C. for 16 h, then hydrolysed by addition of water (50 ml). The hydrolysed mixture was further heated to 70° C. for 1.5 h in order to destroy excess dimethyl sulfate, then diluted with MTBE and worked up as described in Example 1. The crude product was distilled at 0.06 mbar/94-95° C. to yield 8.8 g (77%) of product.

IR (film): 2960 m, 2930 m, 1697 vs, 1323 s, 1132 s, 770 m.
$^1$H-NMR (400 MHz, CDCl3): 4.48-4.20 (m, 1H), 4.00-3.92 (m, 2H), 2.74 (br. s, 3H), 1.58-1.56 (m, 1H), 1.40-1.25 (m, 8H), 1.10 (d, J=7, 6H), 0.92-0.88 (m, 6H).
$^{13}$C-NMR: see Table. MS (EI 70 eV): 229 (<1%, M$^+$), 214 (19), 118 (62), 102 (47), 71 (63), 58 (100).

Odour description: spicy, peppery

EXAMPLE 4

4-Methyl-3-pentyl-oxazolidin-2-one 4.1. 4-Methyl-oxazolidin-2-one (cf. K. Rein et al., *J. Am. Chem. Soc.* 1989, 111, 2211.)

Diethyl carbonate (46.8 g, 397 mmol, 1.2 equiv.) was added to a catalytic amount (1 mol %) of freshly prepared NaOEt (from 76 mg Na and 0.4 ml EtOH). 2-Aminopropanol (24.6 g, 328 mmol, 1 equiv.) was then added and the resulting solution was heated to 125° C. upon which EtOH started to distill. After 5 h the mixture was cooled to room temperature and excess diethyl carbonate was removed in high vacuum 0.5 mbar/50° C. to give 33.0 g (99%) of analytically pure 5-methyloxazolidinone as a pale yellow oil.

IR: 3290 br., 2975 w, 1738 vs, 1481 m, 1238 m, 1029 s, 935 m. $^1$H-NMR (400 MHz, CDCl$_3$): 7.02 (br. s, 1H), 4.50 (t, J=8.2, 1 H), 4.02 (hext, J=4.4, 1 H), 3.93 (dd, J=8.4, 6.4, 1H), 1.28 (d, J=6.4, 3H). $^{13}$C-NMR: 160.0 (s), 71.4 (t), 48.0 (d), 20.3 (q). MS (EI): 101 (27, M+), 86 (100, [M-CH$_3$]+).

4.2. 4-Methyl-3-pentyl-oxazolidin-2-one

4-Methyl-oxazolidin-2-one (18.0 g, 178 mmol) in THF (100 ml) was added slowly via dropping funnel to a slurry of hexane-washed NaH (60% in mineral oil, 7.12 g, 178 mmol, 1.0 quiv.) in THF (400 ml) upon which H$_2$-evolution was observed. Neat iodopentane (70.51 g, 356 mmol, 2.0 equiv.) was added rapidly and the mixture stirred for 1 h at room temperature, then heated to reflux for 60 h. After cooling to 5° C., 2N H$_2$SO$_4$ (180 ml) was slowly added. The mixture was extracted with MTBE and worked up as usual. Distillation over a Widmer-column at 115° C./0.08 mbar afforded the product as a slightly yellow liquid (20.54 g, 73%).

$^1$H-NMR (400 MHz, CDCl$_3$): 4.40 (t, J=8.2, 1 H), 3.89 (hext, J=4.4, 1H), 3.82 (dd, J=8.4, 6.4, 1H), 3.40-3.36 (m, 1H), 3.10-3.03 (m, 1H), 1.65-1.42 (m, 2H), 1.39-1.22 (m 4H), 1.28 (d, J=6.4, 3H), 0.90 (t, J=7.2, 3H). $^{13}$C-NMR: 157.9 (s), 68.7 (t), 50.6 (d), 41.4 (t), 28.7 (t), 26.9 (t), 22.1 (t), 18.0 (q), 13.8 (q). MS (EI): 171 (2, M$^+$), 156 (33), 142 (5), 114 (100, [M-C$_4$H$_9$]$^+$), 102 (10), 86 (15), 70 (52).

Odour description: celery, jasminic

EXAMPLE 5

Preparation of a spicy-woody masculine fragrance

|  | Weight parts |
|---|---|
| Bergamote Ess. | 10 |
| Ethylene Brassylate | 50 |
| Cardamome Graines Ess. | 1 |
| Floralym | 25 |
| Galaxolide 50 PHT | 250 |
| Georgywood | 5 |
| Givescone | 2 |
| Grapefruit Ess | 5 |
| Javanol | 1 |
| Kephalis | 50 |
| Lavance Ess. | 5 |
| Linalool Synt. | 30 |
| Moxalone 50% TEC | 30 |
| Diethylphtalate | 265 |
| Poivre Noir Ess. | 10 |
| Rose Pure Ether MEF | 1 |
| Salicylate Benzyle | 150 |
| Velvione | 10 |
| Total: | 900 |

Addition of 100 weight parts of Dimethylcarbamic acid 1,5-dimethyl-1-vinyl-hex-4-enyl ester (Table 2, compound 22) enhances the spicy-peppery aspect of the fragrance and gives it more overall lift.

The invention claimed is:
1. A method of manufacturing a fragrance application, comprising the incorporation as a fragrance ingredient a tertiary non-vinylic carbamate of formula (I)

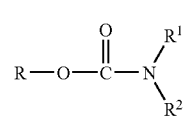

(I)

wherein
R$^1$=R$^2$ and which are selected from the group consisting of:
(a) C$_1$ to C$_{11}$ alkyl; C$_3$ to C$_{11}$ alk-(>1)-enyl; or C$_2$ to C$_{11}$ alkynyl group; and
(b) cycloalkyl optionally substituted with alkyl, alkenyl and alkoxy group(s); C$_3$ to C$_8$ cycloalkenyl optionally substituted with alkyl, alkenyl and alkoxy group(s); or phenyl or naphthyl optionally substituted with alkyl, alkenyl and alkoxy group(s); or
(c) C$_4$ to C$_{14}$ cycloalkylalkyl, wherein the cycloalkyl ring is optionally substituted with alkyl, alkenyl and alkoxy group(s); or phenylalkyl or naphthylalkyl, wherein the aromatic ring is optionally substituted with alkyl, alkenyl and alkoxy group(s); and
R is selected from the group consisting of:
(a) C$_5$ to C$_{11}$ alkyl; C$_3$ to C$_{11}$ alk-(>1)-enyl; or C$_2$ to C$_{11}$ alkynyl group; or
(b) cycloalkyl optionally substituted with alkyl, and alkenyl group(s); C$_3$ to C$_8$ cycloalkenyl optionally substituted with alkyl, and alkenyl group(s); or phenyl or naphthyl optionally substituted with alkyl, and alkenyl group(s); or (c) $C_4$ to $C_{14}$ cycloalkylalkyl, wherein the cycloalkyl ring is optionally substituted with alkyl, and alkenyl group(s); $C_4$ to $C_{14}$ cycloalkenylalkyl, wherein the cycloalkenyl ring is optionally substituted with alkyl, and alkenyl group(s); or phenylalkyl or naphthylalkyl, wherein the aromatic ring is optionally substituted with alkyl, and alkenyl group(s); and (d) heteroaromatic ring optionally substituted with alkyl, alkenyl and alkoxy group(s); heteroarylalkyl ring optionally substituted with alkyl, alkenyl and alkoxy group(s); heterocyclic ring optionally substituted with alkyl, alkenyl and alkoxy group(s) or heterocycloalkyl ring optionally substituted with alkyl, alkenyl and alkoxy group(s), and the ring having 5 to 6 ring members and the hetero atom of the ring is nitrogen; and R, $R^1$ and $R^2$ having together 7 to 18 carbon atoms, and further wherein the fragrance ingredient is a fragrance exhibiting odours selected from a spicy range, an herbaceous range or a floral-rosy range.

2. A compound of formula (I)

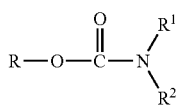
(I)

wherein the compound exhibits odours selected from a spicy range, an herbaceous range or a floral-rosy range, and further wherein the groups R, $R^1$ and $R^2$ are selected according to the following table:

| R | $R^1$ | $R^2$ |
| --- | --- | --- |
| hex-3-enyl | ethyl | ethyl |
| 2-ethyl-hexyl | methyl | methyl |
| 3-methyl-but-2-enyl | ethyl | ethyl |
| 3-methyl-but-3-enyl | ethyl | ethyl |
| 2,2,5-trimethyl-hex-4-enyl | ethyl | ethyl |
| undec-10-enyl | methyl | methyl |
| 1,1-dimethyl-(4-methyl-cyclohex-3-enyl)-ethyl | methyl | methyl |
| 1,1-dimethyl-(4-methyl-cyclohex-3-enyl)-methyl | methyl | methyl |
| 1,2-dimethyl-1-propyl-propyl | methyl | methyl |
| 1,2-dimethyl-1-propyl-iso-propyl | methyl | methyl |
| furylmethyl | ethyl | ethyl. |

3. A method of manufacturing a fragrance application according to claim 1, wherein the fragrance application is selected from the group consisting of perfume, household product, laundry product, body care product and cosmetics.

4. A method of manufacturing a fragrance application according to claim 1, wherein the fragrance ingredient is a compound selected from a compound according to formula (I)

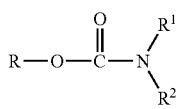
(I)

wherein the groups R, $R^1$ and $R^2$ are selected according to the following table:

| R | $R^1$ | $R^2$ |
| --- | --- | --- |
| hex-3-enyl | ethyl | ethyl |
| 2-ethyl-hexyl | methyl | methyl |
| 3-methyl-but-2-enyl | ethyl | ethyl |
| 3-methyl-but-3-enyl | ethyl | ethyl |
| 2,2,5-trimethyl-hex-4-enyl | ethyl | ethyl |
| undec-10-enyl | methyl | methyl |
| 1,1-dimethyl-(4-methyl-cyclohex-3-enyl)-ethyl | methyl | methyl |
| 1,1-dimethyl-(4-methyl-cyclohex-3-enyl)-methyl | methyl | methyl |
| 1,2-dimethyl-1-propyl-propyl | methyl | methyl |
| 1,2-dimethyl-1-propyl-iso-propyl | methyl | methyl |
| furylmethyl | ethyl | ethyl. |

5. A method of manufacturing a fragrance application according to claim 1, wherein the fragrance ingredient is a compound selected from the group consisting of

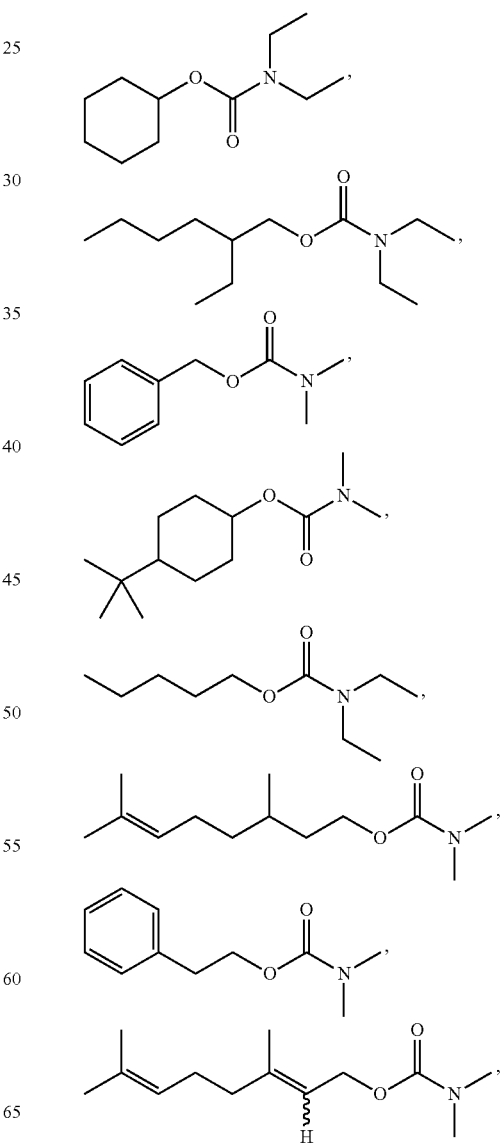

-continued

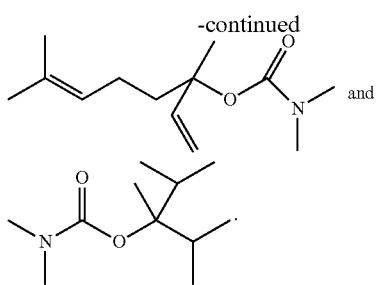

and

6. A method of manufacturing a fragrance application according to claim 5, herein the fragrance application is selected from the group consisting of perfume, household product, laundry product, body care product and cosmetics.

7. A method of manufacturing a fragrance application according to claim 4, wherein the fragrance application is selected from the group consisting of perfume, household product, laundry product, body care product and cosmetics.

8. A method of manufacturing a fragrance application, comprising the incorporation as fragrance ingredient of a compound of formula (I) according to claim 2.

9. A method of claim 8 wherein the fragrance application is selected from the group consisting of perfume, household product, laundry product, body care product and cosmetics.

* * * * *